United States Patent [19]

Logue et al.

[11] Patent Number: 4,887,590

[45] Date of Patent: Dec. 19, 1989

[54] JOINT SUPPORT FOR UNDERWATER USE OR FOR USE IN A WET ENVIRONMENT

[76] Inventors: Brian V. Logue, 7 Roosevelt St., Bayville, N.Y. 11709; Theodore J. Rusnack, 22 Pound Hollow Ct., Old Brookville, N.Y. 11545

[21] Appl. No.: 211,137

[22] Filed: Jun. 22, 1988

Related U.S. Application Data

[63] Continuation of Ser. No. 4,917, Jan. 20, 1987, abandoned.

[51] Int. Cl.$^4$ .............................................. A61F 5/00
[52] U.S. Cl. .................................. 128/80 C; 128/80 F
[58] Field of Search ....................... 2/2.1 R, 2.1 A, 2.5, 2/44, 45, DIG. 5, 135; 128/80 F, 80 C, 88

[56] References Cited

U.S. PATENT DOCUMENTS

| | | | |
|---|---|---|---|
| 3,074,400 | 1/1963 | Schulman | 128/80 C |
| 3,786,804 | 1/1974 | Lewis | 128/80 C |
| 4,041,940 | 8/1977 | Frankel et al. | 128/80 C |
| 4,060,075 | 11/1977 | Blomer et al. | 128/90 |
| 4,064,874 | 12/1977 | Valin | 128/80 C |
| 4,084,584 | 4/1978 | Detty | 128/80 C |
| 4,084,586 | 4/1978 | Hettick | 128/157 |
| 4,130,115 | 12/1978 | Taylor | 128/80 C |
| 4,407,276 | 10/1983 | Bledsoe | 128/80 C |
| 4,572,170 | 2/1986 | Cronk et al. | 128/80 C |
| 4,628,916 | 12/1986 | Lerman et al. | 128/80 C |
| 4,643,176 | 2/1987 | Mason et al. | 128/80 C |
| 4,697,583 | 10/1987 | Mason et al. | 128/80 F |

FOREIGN PATENT DOCUMENTS 2110067 6/1985 United Kingdom ............. 2/DIG. 5

OTHER PUBLICATIONS

1. Soft Goods Catalogue—Donjoy.
2. The 4-Point Knee Brace—Donjoy.
3. The Combined Instabilities, Knee Brace, Donjoy.
4. RKS Rotatory Knee Stabilizer—Donjoy.
5. 4-Point ACL Sport Knee Brace—Donjoy.
6. Clinical Evaluation of the 4-Point ACL Brace, A Preliminary Report of Phase One by Skyhar, M.D., and P. W. Cauley, O.P.A., R.T.—Donjoy.
7. System 2—Donjoy.
8. Protective Knee Guard—Donjoy.

*Primary Examiner*—Edgar S. Burr
*Assistant Examiner*—Huong Q. Pham
*Attorney, Agent, or Firm*—Hoffmann & Baron

[57] ABSTRACT

A water-resistant device for providing support to a joint of an articulable portion of a limb, and adapted for use in and out of water. The water resistance device includes a pliable enclosure member having a continuous substantially tubular contour, for placement over the limb and surrounding the joint thereof. The pliable enclosure member is water resistant and permits a minimal degree of water absorption as to exhibit buoyancy and substantially maintain its intrinsic mass upon being exposed to water. The water resistant device includes a joint support means that is associated with the pliable enclosure member. The joint support means is fixedly positioned with respect to the pliable enclosure to provide to the joint, support against both lateral and torsional forces imposed thereon during use in and out of the water. Retaining means is also provided which is associated with the pliable enclosure member and the joint support means as to (i) to releasably fasten the pliable enclosure member and associated joint support means to the articulable portion of the limb, (ii) to facilitate desired relative positioning of the pliable enclosure member and the associated joint support means about the joint, and (iii) to prevent longitudinal displacement of the pliable enclosure member along the limb during use in and out of water.

28 Claims, 2 Drawing Sheets

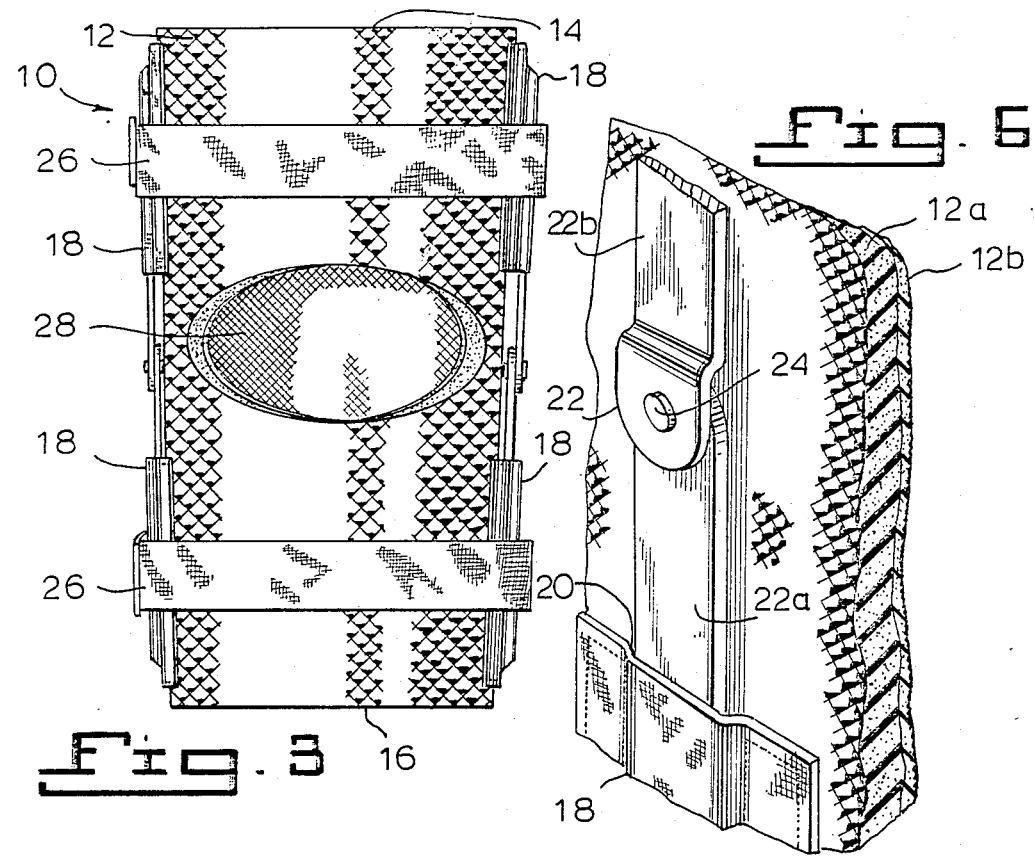
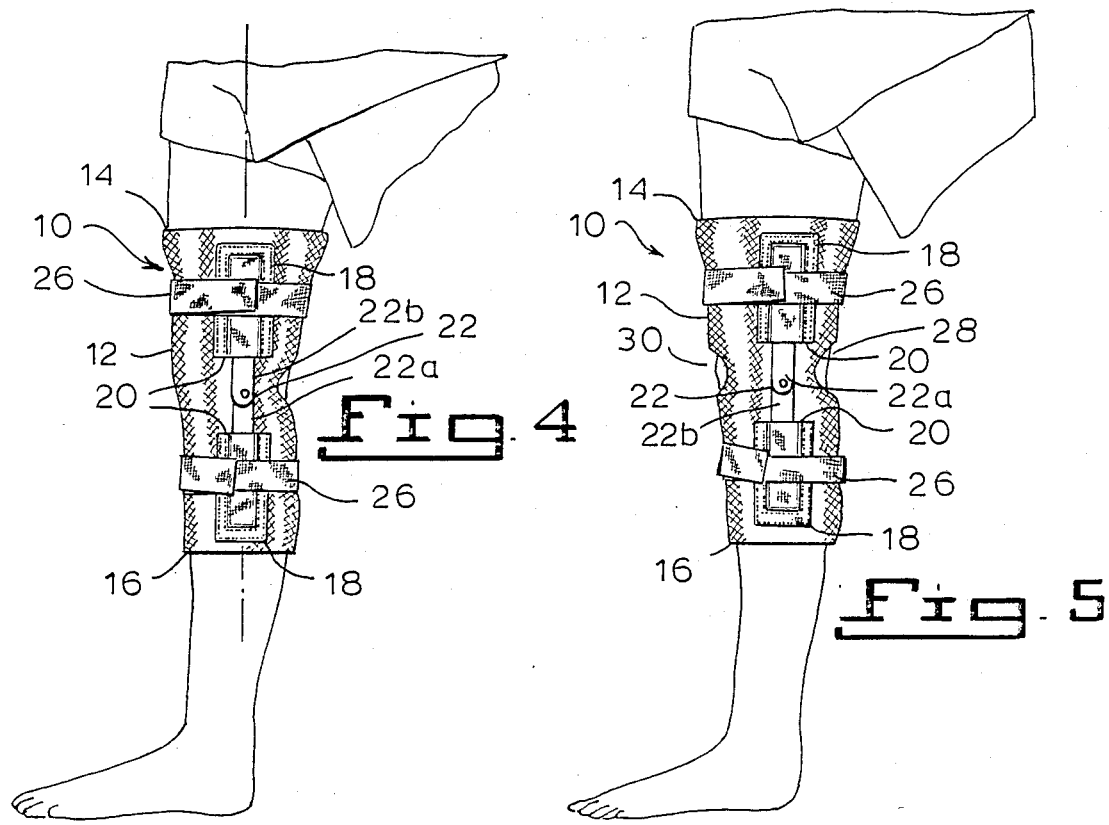

JOINT SUPPORT FOR UNDERWATER USE OR FOR USE IN A WET ENVIRONMENT

This is a continuation of application Ser. No. 004,917 filed Jan. 20, 1987, now abandoned.

BACKGROUND OF THE INVENTION

The present invention relates generally to a joint support or brace and, more particularly, to a joint support which is capable of being used underwater or in a wet environment.

Perhaps one does not appreciate the amount of support provided by the knee until it becomes injured or impaired. The knee is the largest joint of the body and must support the entire weight of the upper body during the normal course of walking, running and other activities. Injuries to the knee are serious, due not only to the fact that the knee plays a major part in the normal human gait but, since the knee must support great stresses, such stresses may aggravate any injury and prolong the healing process, unless the injured person can keep all weight off the knee as, for example, by using crutches or remaining in traction until healing is completed. Most people, however, do not prefer to remain immobile until the healing process is completed. Moreover, a certain degree of exercise for the patient's muscles is encouraged in order to prevent them from becoming unreasonably weak through lack of use. However, a physician may wish to restrict certain types of leg motion or to provide support to the knee until some damaged tissue has healed itself. As such, orthopedic devices are made available to provide support to the knee, or similarly, to other joints such as the elbow, during the healing process. Various devices have been developed to restrict the knee, especially during normal knee movements in the practice of athletics. These devices are used on injured, unhealthy or congenital knee problems which exhibit atrophy or weakness. As stated earlier, such devices are also available to restrict motion of, and provide support to, other joints such as the elbow.

Orthopedic devices of this general character have been developed in the past for the primary purpose of holding the leg or arm of a patient in a rigid posture, particularly during the recovery interval following surgery on the knee or elbow joint. In addition to providing post-surgical support, such devices have been used to provide support to a knee or elbow which has been weakened because of torn ligaments, torn cartilage, arthritis and the like.

Some of the previous supportive devices have made extensive use of heavy duty elastic material to provide support for the knee. One such device is described in U.S. Pat. No. 3,786,804 to Lewis. This device includes a main body in the form of an elastic cylindrical sleeve. Support is also provided by metal arms associated with the elastic sleeve, as well as, by an arrangement of pads also associated with said sleeve. Another elastic supportive device is described in U.S. Pat. No. 4,064,874 to Valin. This device employs steel members, which are used to provide lateral support to the knee.

Another of the known knee supports has been described in U.S. Pat. No. 4,084,584 to Detty, which illustrates a knee sleeve comprising a front section, a rear panel and a restrictor pad. The front section and rear panel are described as being fabricated from neoprene.

Other joint supportive devices have been described in U.S. Pat. No. 4,407,276 to Bledsoe, which shows a brace for articulated limbs comprised essentially of two flexible sheets of cushioned material; U.S. Pat. No. 4,084,586 to Hettick, which shows a tubular support for enclosing a body member comprising a stretchable elastic member having facings which possess a relatively low coefficient of friction; U.S. Pat. No. 4,042,940 to Frankel et al., which shows a contoured knee immobilizer comprised of three substantially rigid shells and foamed cushions; and U.S. Pat. No. 3,074,400 to Schulman, which illustrates a knee cap brace, which employs plastic or metallic stays to provide support.

While all of these various devices may have solved one or more special problems, none of the devices have been offered for use underwater or in a wet environment. Thus, athletes who partake in activities such as swimming, surfing, skin diving, water skiing and the like, are prevented from doing so during the post-surgical healing stage of the joint or during a time period when the joint has become injured or weakened, since a joint support which can be used underwater or in a wet environment has heretofore been unavailable. Similarly, until now, a person was unable to shower or bathe with the aid of a knee support and, unfortunately, knee injuries have been compounded, since a weakened knee, unaided by a supportive device, is unable to tolerate the stress required to support a person who wishes to stand upright in a shower. Such stress will only cause a knee injury to become aggravated or, even worse, can cause a person to slip while entering a bath tub, which can result in a serious injury.

Additionally, none of the supportive devices which are currently available can be used by a patient undergoing whirlpool therapy.

The knee supports currently available are structurally deficient for the use contemplated by the present invention for a variety of reasons. First, if the materials generally used in fabricating the currently available supportive devices are caused to become wet, the entire supportive device will become unreasonably heavy, thereby producing an added stress on the joint. Second, this additional weight will invariably cause the knee to become less buoyant in the water and, as a result, a swimmer would have to use injured muscles just to keep the knee afloat. Furthermore, the materials generally used will gradually, and in some instances, rapidly deteriorate with repeated exposure to water, especially salt water. Thus, the durability and life of the supportive device is drastically minimized. Another noted deficiency of the supportive devices currently available is observed in their construction, which results in a device that is incompatible with the intended use of the present device. Specifically, many of the known devices are structurally too cumbersome for underwater use. One of the negative effects of cumbersome construction is the lack of comfort experienced by the user. Moreover, as the supportive device becomes wet, it has a tendency to become vertically displaced along the arm or leg. As such, the device can become disassociated from the joint and will fail to provide the support required. This results in the user being required to regularly make adjustment to the device, which impedes his or her ability to partake in the intended activity.

Accordingly, it is a primary object of the present invention to provide a joint support which is capable of being used underwater or in a wet environment.

It is another object of the present invention to provide a joint support that maintains its weight when it becomes wet.

It is a further object of the present invention to provide a joint support that is buoyant.

It is still another object of the present invention to provide a joint support that is durable and, which will maintain its integrity after prolonged and repetitive exposure to water, especially salt water.

It is yet a further object of the present invention to provide a joint support which maintains its position about the knee or elbow area while being used.

It is another object of the present invention to provide a joint support which is structurally non-cumbersome.

SUMMARY OF THE INVENTION

In accordance with the foregoing objects and advantages the present invention, in brief summary, relates to a water resistant joint supporting device adapted for in and out of water use comprising:

a pliable enclosure member for substantially enclosing said joint, said pliable enclosure member being fabricated from an elastomeric material which is substantially resistant to water;

supporting means associated with said pliable enclosure member;

securing means associated with said pliable enclosure member and said supporting means to releasably fasten the device to a joint; and said securing means, supporting means and pliable enclosure member being arranged so that, when said device is fastened to the joint, the supporting means and pliable enclosure member will be positioned in the desired location to provide maximum support to the joint without unduly restraining mobility, and the securing means will be positioned to facilitate retention and desired relative positioning during use in and out of the water.

In one embodiment of the present invention the pliable enclosure member is fabricated from a unitary sheet of neoprene rubber. In another embodiment, the pliable enclosure member is fabricated from an inner and outer layer of neoprene rubber, wherein the inner layer is fabricated from a lighter or softer type of neoprene relative to the outer layer.

BRIEF DESCRIPTION OF THE DRAWINGS

FIG. 3 is a rear view of the present knee supporting device illustrating a cut-out in the rear portion;

FIG. 4 is a side view of the present knee supporting device being worn by a user;

FIG. 5 is a side view of the present knee supporting device being worn by a user, illustrating a front opening and a cut-out in the rear portion; and FIG. 6 is a perspective view of a preferred hinge arrangement in accordance with the present invention.

DESCRIPTION OF THE PREFERRED EMBODIMENT

Figure 1:
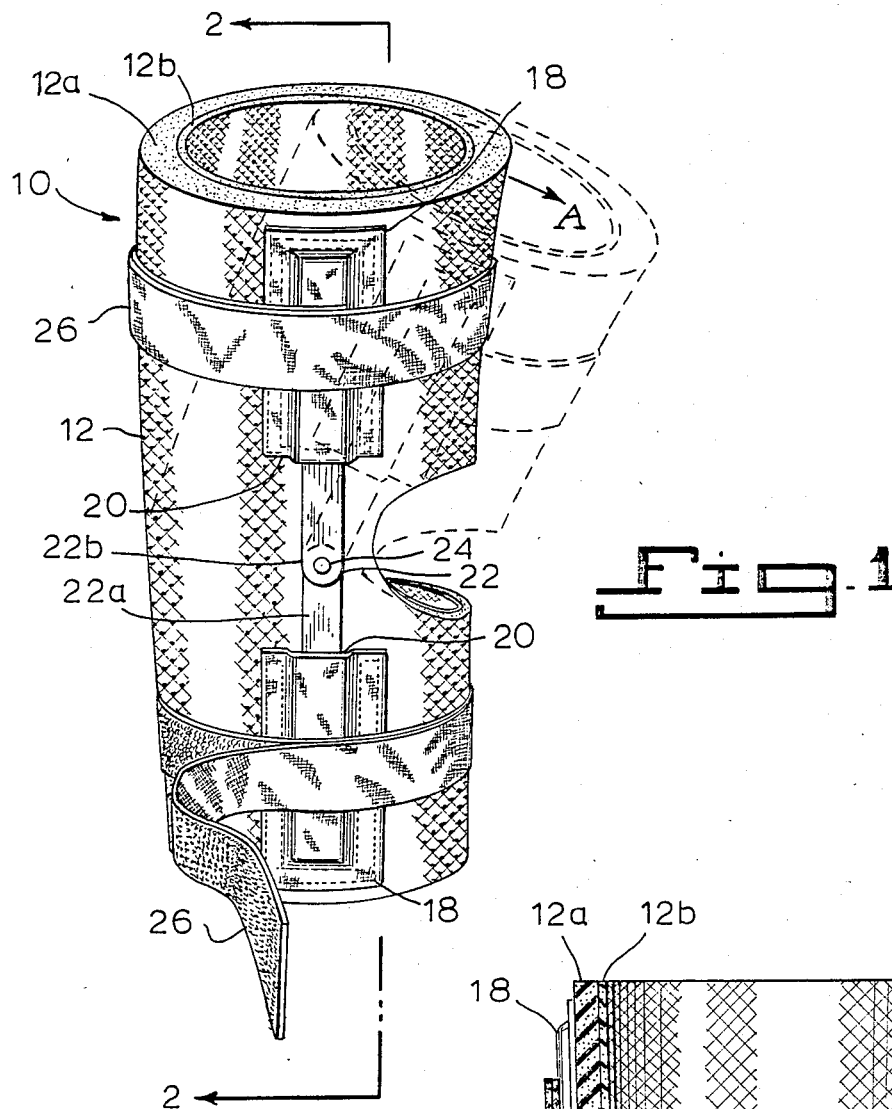
FIG. 1 is a side view of the present joint supporting device and, in particular, a knee supporting device illustrating its flexion capabilities.

The present joint supporting device will effectively provide stability and support, especially ligamentous-type support, to an injured or weakened joint.

Advantageously, the present device is capable of being used underwater or in a "wet environment." For purposes of this description underwater use of the present device is intended to include those situations where the device is worn around the knee or elbow and where the knee or elbow and the device become either partially or totally submerged in water. Use of the device in a "wet environment" is intended to include those situations where the knee or elbow of the user and/or the present device come into contact with water, without necessarily becoming partially or totally submerged in water. Thus, for illustrative purposes only, underwater use or, use in a wet environment can include use by a patient undergoing whirlpool therapy, water skiing, scuba diving, swimming, surfing, sailing, showering, bathing and the like.

The present device also provides stability and support in a "dry" environment. A "dry" environment is intended to include those situations where the device is used in surroundings other than underwater or in a wet environment. As an illustration, the present device can be used while cycling, walking and the like. For arthritis patients, the present device can retain the body heat at the locus of the knee, while supporting the knee, due to the overall structure.

Referring now to the drawings, shown is a knee supporting device 10, including, among other things, a pliable enclosure 12, which constitutes the main body of the device. Pliable enclosure 12, in one embodiment, is unitary and is fabricated from an elastomeric material that is resistant to water. Water resistant, in the context used herein, does not necessarily mean that the elastomeric material must be absolutely impervious to water. Rather, the material can tolerate a certain minimal degree of water absorption or penetration. However, the elastomeric material must possess characteristics which will not permit more than minimal amounts of water to be absorbed or penetrated. Thus, the elastomeric material must be capable of substantially preventing passage and absorption of water and, must be capable of maintaining its integrity after prolonged and repeated exposure to water. Naturally, the elastomeric material can be such that it is completely resistant to water. Preferably, the elastomeric material used to fabricate pliable enclosure 12 is neoprene. Neoprene which is useful in this regard is commercially available from the Rubatex Corporation, P.O. Box 340, Bedford, VA 24523.

It has been discovered that when pliable enclosure 12 is at least one quarter of an inch thick, the most efficient and preferable knee supporting device is fabricated. Pliable enclosure 12 achieves a substantially cylindrical or tubular contour, to effectuate substantial enclosure of the knee. Formation of the specific contour is accomplished by rolling a piece of the elastomeric material upon itself, and thereafter, by bonding its opposed edges one to the other (not shown). An elastomeric adhesive is suitable to effectuate the bond. Preferably, the elastomeric adhesive is neoprene cement.

Figure 2:
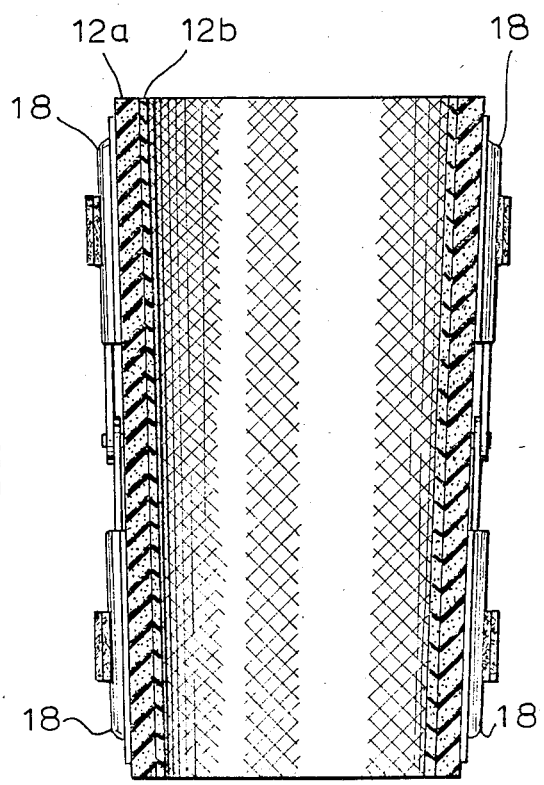
FIG. 2 is a sectional view of the present knee supporting device taken along lines 2—2 of FIG. 1.

In an alternate and preferred embodiment, pliable enclosure 12 is fabricated from two separate neoprene portions, an outer portion 12a and an inner portion 12b, which are best illustrated in FIGS. 1, 2 and 6. Outer portion 12a is fabricated from the types of elastomeric materials which have been heretofore described. Inner portion 12b is fabricated from a softer and lighter elastomeric material, relative to outer portion 12a. Inner portion 12b can also be fabricated from the same material as outer portion 12a. Inner portion 12b is adhesively associated with outer portion 12a. Adhesion of inner portion 12b to outer portion 12a can be accomplished in any conventional manner, and is preferably accomplished by using a neoprene cement. When the knee supporting device 10 is worn by a user, inner portion 12b increases the overall comfort experienced by the user and, moreover, participates in preventing the device 10 from becoming vertically displaced along the leg during use, because of the gripping effect it has on the leg.

The vertical length of pliable enclosure 12 should be sufficient so that when the device 10 is placed on the leg of the user, upper end 14 is disposed proximate the mid-thigh area and lower end 16 is disposed proximate the mid-calf area, as can be seen in FIGS. 4 and 5.

Associated with pliable enclosure 12 are pocket members 18. Pocket members 18 can be fabricated from any suitable material, but, are preferably fabricated from canvas or a heavy nylon. As illustrated, pocket members 18 are mounted on opposed sides of pliable enclosure 12. The mounting of pocket members 18 to pliable enclosure 12 can be accomplished by any conventional means, but, bearing in mind one proviso, the adhesive bond or stitching must be capable of maintaining its composition and integrity when subjected to contact with water. Thus, in a preferred embodiment, pocket members 18 are stitched onto pliable enclosure 12 with a heavy nylon thread. Pocket members 18 are stitched on three sides, thereby creating an opening 20, which is adapted to slidably receive support member 22. Opening 20 is dimensioned just slightly larger than support member 22, with respect to width and thickness, so that opening 20 can accommodate opposed ends of support member 22, thereby minimizing or eliminating any horizontal displacement of support member 22 within opening 20. Each of the pocket members 18 should laterally extend about 2 inches and longitudinally extend about 5 inches along the outer surface of pliable enclosure 12. Preferably, pocket members 18 should be situated on pliable enclosure 12 in a manner which would permit opposed ends (not shown) of support member 22 to be situated about 1 inch away from each respective end 14, 16 of the device. The number of pocket members used is proportionate to the number of support members to be used and, as such, for each support member used, two pocket members should be used.

Support member 22 is intended to provide support against any lateral or torsion forces and, essentially includes two rigid bars 22a, 22b. Rigid bars 22a and 22b are preferably fabricated from stainless steel or aluminum. Most preferably, they are fabricated from stainless steel. These types of materials will result in a support member which is rigid enough to resist torsion and bending loads. Rigid bars 22a, 22b should be adequately dimensioned so that, in tandem, they will provide adequate support to the knee. Merely for illustrative purposes, it has been discovered that adequate support is attained when the rigid bars used each have a length of 6½ inches, a width of ¾ of an inch and a thickness of ⅛ of an inch. Rigid bars 22a, 22b are pivotably associated with each other by means of pin 24. Pin 24 extends through two apertures (not shown), one being disposed on the end of rigid bar 22a and the other on the end of rigid bar 22b, thereby forming a hinge, which permits flexion extension of support member 22 in the direction of arrow A shown in FIG. 1. Rigid bars 22a, 22b are arranged in vertical alignment with respect to each other, when the user is standing upright, as can be seen in FIGS. 4 and 5. As shown, support member 22 remains unflexed when the user's knee is unflexed. Advantageously, the support member will remain unflexed even when the knee becomes slightly flexed (not shown). This will permit the device to provide maximized support during such situations. FIGS. 4 and 5 also illustrate pliable enclosure 12 and support member 22 being positioned at the most desired location, that is, with the hinge formed by pin 24 being positioned adjacent the knee of the wearer. Such positioning further allows rigid bars 22a, 22b to provide maximum support to the knee.

Referring particularly to FIG. 6, illustrated is an alternate and preferred hinge arrangement. The apertured portion of rigid bar 22b is illustrated as being out of vertical alignment with the remainder of the bar, at the proximity of the hinge formed by pin 24, thereby creating an "offset hinge". Such an arrangement will increase the strength of support member 22, particularly, at the locus of pin 24. Although only one of the rigid bars (22b) is illustrated to include a vertically unaligned end, it is to be understood that an "offset hinge" can comprise both rigid bars 22a, 22b each of which includes one end that is vertically unaligned for imparting increased strength to support member 22.

Referring, once again generally to the drawings, also illustrated are retaining straps 26, which can best be seen in FIGS. 1, 4 and 5. Retaining straps 26 are employed to fasten the present device around the leg of a user. Additionally, retaining straps 26 alone, or in cooperation with inner portion 12b of pliable enclosure 12, prevent the device from becoming vertically displaced along the leg of a user. As illustrated, retaining straps 26 are of the VELCRO, which is the preferable means for securing the device 10 around the leg of a user, due to the simplicity and ease of adjustment associated with the use of VELCRO. It is to be understood, however, that other means for securing device 10 around the leg of a user, by way of retaining straps 26, are also within the scope of the present invention. Additionally, a preferred embodiment of the present device would include two, 2 inch VELCRO retaining straps 26, which extend entirely around the leg of the user. Complete extension around the leg assists in preventing any vertical displacement along the leg and also provides an additional degree of support, since straps 26 overlap pocket members 18 and pliable enclosure member 12 and, as such, pull support member 22 against the knee, as they become fastened. Moreover, such positioning of straps 26 will facilitate retention of the device to the user's knee, while maintaining the desired positioning of device around the knee.

Referring now to FIG. 3, also shown is cut-out portion 28 located at a point which corresponds to the back of a wearer's knee, which point is substantially equidistant from upper end 14 and lower end 16, when the device is worn by a user. Although cut-out portion 28 is not essential to the present invention, it is preferable to include it as part of the overall arrangement, since it will prevent any gathering of pliable enclosure 12, which may occur in an area proximate the back of the wearer's knee upon simultaneous flexion of the knee and the device 10. The elimination of the gathering provides increased comfort to the user when the device 10 is worn.

Referring now to FIG. 5, shown is opening 30 which is circumferentially associated with the user's patella. Device 10 can optionally include opening 30 when a use is unable to tolerate any undue pressure on the patella. Opening 30 is also desirable to prevent, or to aid in the prevention of, lateral movement of the patella, which can occur as the knee is flexed and extended.

Finally, the present device can include a v-shaped cut-out (not shown) proximate upper end 14 or lower end 16. The v-shaped cut-out can be used if the device ever becomes too tight and, hence, uncomfortable about the user's thigh or calf. The v-shaped cut-out will not effect the stability or supportive capabilities of the present invention, and is merely intended fo provide increased comfort when necessary.

In an alternate embodiment, the present joint supporting device can be used to provide support to the elbow. Although not illustrated, it is to be understood that where the present device is to be used as an elbow support, the device will include the same structural elements disclosed hereinabove. Naturally, the dimensions of the structural elements will be somewhat reduced, relative to those dimensions disclosed hereinabove, when the device is to be used as an elbow support, since the elbow is a smaller joint than the knee.

Thus, in accordance with the foregoing description, a device is made available to support the knee or elbow, which can be used underwater or in a wet environment. The present device is particularly appropriate for a swimmer, since the device possesses properties which make it buoyant and allow it to maintain its light weight.

While preferred embodiments and several variations of the present invention are described in detail herein, it should be apparent that the disclosure and teachings of the present invention will suggest many alternative designs to those skilled in the art.

What is claimed is:

1. A method for providing support to a knee or elbow joint while engaging in aquatic activities, comprising:
    (a) providing a buoyancy to said joint when immersed in water, said buoyancy being provided by providing a pliable enclosure having a continuous substantially tubular contour made from an elastomeric material which substantially prevents passage and absorption of water, including neoprene rubber for placement over the knee or elbow joint and surrounding said joint, the pliable enclosure further including,
        (i) a joint supporting means associated with the pliable enclosure, being fixedly positionable with respect to the pliable enclosure to provide support against both lateral and torsional forces imposed on the joint during use, including when entering the water, in the water, and leaving the water, and
        (ii) retaining means associated with the pliable enclosure and said joint supporting means to allow the fastening and unfastening of the pliable enclosure and associated joint supporting means to a limb, such as the leg or arm of the user, above and below the joint, and to facilitate the positioning of the pliable enclosure and associated joint supporting means about the joint to prevent longitudinal displacement of the pliable enclosure and associated joint supporting means on the limb when said retaining means is secured about the joint during use;
    (b) placing the pliable enclosure and the associated joint supporting means on the limb of the user, about the joint which requires support;
    (c) aligning the joint supporting means on either side of the joint to allow the flexing and unflexing of the joint in alignment with the flexing and unflexing of said pliable enclosure and said joint supporting means;
    (d) fastening said retaining means on the limb above and below the joint to secure the pliable enclosure end associated joint supporting means about the joint to prevent longitudinal displacement of the pliable enclosure along the limb of the user during use; and,
    (e) engaging in aquatic activities.

2. The method recited in claim 1, further comprising: releasing said retaining means after use to allow removal of said pliable enclosure from the limb of the user, and then removing said pliable enclosure from the limb of the user.

3. The method of claim 2, wherein step (a) further comprises providing said pliable enclosure having an inner layer of an elastomeric material and an outer layer of an elastomeric material bonded over said inner layer, said inner layer having a consistency which resists longitudinal displacement along the limb of the user during use.

4. The method of claim 1, wherein step (a) further comprises providing said pliable enclosure made from said elastomeric material having a thickness of at least about ¼ of an inch.

5. The method of claim 1, wherein step (a) further comprises providing said joint supporting means associated with said pliable enclosure which includes two pairs of pivotally connected rigid bars, each pair of said pivotally connected bars disposed on each side of said pliable enclosure for alignment about the joint of the user.

6. The method of claim 5, wherein step (a) further includes inserting opposed ends of said pairs of pivotally connected bars slidably within pockets associated with the pliable enclosure to fixedly secure the opposed ends of the pairs of pivotally connected bars to said pliable enclosure.

7. The method of claim 6, wherein step (a) further includes providing said pliable enclosure with said pockets stitched to said pliable enclosure by nylon thread.

8. The method of claim 5, wherein step (a) further includes providing said rigid bars fabricated from a material selected from the group consisting of aluminum and stainless steel.

9. The method of claim 8, wherein step (a) further includes providing said pairs of rigid bars, each pivotally connected by a pin which extends through an aperture disposed on each bar.

10. The method of claim 6, wherein step (a) further includes providing said retaining means which includes a pair of retaining straps, one of said retaining straps encircling said pliable enclosure and said pockets receiving said rigid bars above said joint, and the other retaining strap encircling said pliable enclosure and said pockets receiving said rigid bar below said joint, as to adapt said rigid bars to resist outward deflection away from said joint as said limb moves about said joint from an extended position to a flexed position.

11. The method of claim 1, wherein step (a) further comprises providing said retaining means including retaining straps, the end portion of which is fabricated from VELCRO fastening material, said retaining straps being of suitable length for extension circumferentially around said pliable enclosure and said associated joint supporting means when said enclosure is placed over said limb about said joint.

12. The method of claim 1, wherein step (a) further comprises providing said pliable enclosure with a cut-out portion disposed proximate the rear of said joint, behind said joint when said pliable enclosure is placed over said limb and about said joint.

13. The method of claim 1, wherein step (a) further comprises providing said pliable enclosure having the configuration to conform to the anatomy of the knee portion of a leg for placement about the said knee joint.

14. The method of claim 13, wherein step (a) further comprises providing said pliable enclosure with an opening disposed on its front portion, said opening being circumferentially associated with a patella of the knee when said pliable enclosure is placed over the knee of the leg of the user about the knee joint.

15. The method of claim 1, wherein step (a) further comprises providing said pliable enclosure having the configuration to conform to the anatomy of an elbow portion of the arm for placement about the elbow joint.

16. A brace for providing support to a knee or elbow joint while engaging in aquatic activities consisting of:
(a) means to provide buoyancy to said joint when immersed in water, said means comprising a pliable enclosure having a continuous substantially tubular contour made from an elastomeric material which substantially prevents passage and absorption of water, including neoprene rubber for placement over a knee or elbow joint and surrounding said joint, said pliable enclosure having pockets associated therewith;
(b) a joint supporting means associated with said pliable enclosure, said joint supporting means consisting of two pairs of pivotally connected rigid bars, said rigid bars being fixedly positionable with respect to said pliable enclosure, opposed ends of said pairs of pivotally connected bars are slidably received by, and accommodated within said pockets associated with said pliable enclosure in order to provide support against both lateral and torsional forces imposed on the joint during use, including entering the water, in the water, and leaving the water; and,
(c) retaining means associated with the pliable enclosure and said joint supporting means to allow the fastening and unfastening of the pliable enclosure and associated joint supporting means to a limb of the user, above and below the joint, and to facilitate the positioning of the pliable enclosure and associated joint supporting means about the joint to prevent longitudinal displacement of the pliable enclosure and associated joint supporting means on the limb when said retaining means is secured about the joint during use.

17. The brace of claim 16 wherein said pliable enclosure comprises an inner layer of an elastomeric material and an outer layer of an elastomeric material bonded over said inner layer, said inner layer having a consistency which resists longitudinal displacement along the limb of the user during use.

18. The brace of claim 16, wherein the elastomeric material has a thickness of at least about ¼ of an inch.

19. The brace of claim 16, wherein each pair of said pivotally connected rigid bars of said joint supporting means being disposed on each side of said pliable enclosure for alignment about the joint of the user.

20. The brace of claim 16, wherein said pockets are stitched to said pliable enclosure by nylon thread.

21. The brace of claim 19, wherein said rigid bars are fabricated from material selected from the group consisting of aluminum and stainless steel.

22. The brace of claim 21, wherein said rigid bars are pivotally connected to each other by a pin which extends through an aperture disposed on each bar.

23. The brace of claim 16, wherein said retaining means comprises a pair of retaining straps, one of said retaining straps encircling said pliable enclosure and said pockets receiving said rigid bars above said joint and the other retaining strap encircling said pliable enclosure and said pockets receiving said rigid bar below said joint, as to adapt said rigid bars to resist outward deflection away from said joint as said limb moves about said joint from an extended position to a flexed position.

24. The brace of claim 16, wherein said retaining means comprises retaining straps, the end portion of which is fabricated from VELCRO fastening material, said retaining straps being of suitable length for extension circumferentially around said pliable enclosure and said associated joint supporting means when said pliable enclosure is placed over said limb about said joint.

25. The brace of claim 16, wherein said pliable enclosure further comprises a cut-out portion disposed proximate the rear of said joint, behind said joint when said pliable enclosure is placed over said limb and about said joint.

26. The brace of claim 16, wherein said pliable enclosure has the configuration to conform to the anatomy of the knee portion of a leg for placement about the knee joint.

27. The brace of claim 26, wherein said pliable enclosure further includes an opening disposed on its front portion, said opening being circumferentially associated with a patella of the knee when said pliable enclosure is placed over the knee of the leg of the user about the knee joint.

28. The brace of claim 16, wherein said pliable enclosure has the configuration to conform to the anatomy of an elbow portion of the arm for placement about the elbow joint.

* * * * *